United States Patent [19]
McIntyre et al.

[11] Patent Number: 5,604,811
[45] Date of Patent: Feb. 18, 1997

[54] STETHOSCOPE AND HEADSET SYSTEM

[76] Inventors: Kenneth M. McIntyre; Constance T. McIntyre, both of 102 Arcadia Pl., apt. 808, San Antonio, Tex. 78209

[21] Appl. No.: 314,669

[22] Filed: Sep. 29, 1994

[51] Int. Cl.⁶ .................................................... A61B 7/04
[52] U.S. Cl. .............................................. 381/67; 381/86
[58] Field of Search ........................................ 381/67, 86

[56] References Cited

U.S. PATENT DOCUMENTS

| | | | |
|---|---|---|---|
| 4,226,248 | 10/1980 | Manoli | 381/67 |
| 4,254,302 | 3/1981 | Walshe | 381/67 |
| 4,598,417 | 7/1986 | Deno | 381/67 |
| 4,618,986 | 10/1986 | Hower | 381/67 |
| 4,941,187 | 7/1990 | Slater | 381/86 |
| 5,467,775 | 11/1995 | Callahan | 381/67 |

*Primary Examiner*—Curtis Kuntz
*Assistant Examiner*—Minsun Oh

[57] ABSTRACT

A stethoscope and headset system comprising a stethoscope having a monitor mechanism for monitoring internal bodily vibrations of a patient and conversion circuitry coupled to the monitor mechanism for receiving the internal bodily vibrations and transmitting internal bodily indication signals based upon the internal bodily vibrations, a headset having a headband, a pair of earpieces coupled to the headband, a microphone for receiving a user's voice and transmitting a plurality of intercom signals; and a pair of speakers with each speaker coupled to an earpiece for transmitting audible sounds upon actuation by internal bodily indication signals and intercom signals; and a user-orientable selector switch coupled with the stethoscope and headset and coupleable with an intercom system of an aircraft, the selector switch having one orientation for enabling a user to listen to a patient's internal bodily vibrations and another orientation for enabling a user to communicate through the intercom system.

1 Claim, 4 Drawing Sheets

STETHOSCOPE AND HEADSET SYSTEM

BACKGROUND OF THE INVENTION

1. Field of the Invention

The present invention relates to a stethoscope and headset system and more particularly pertains to allowing a crew member of an aircraft to monitor a patient's internal bodily vibrations and communicate with other crew members through an aircraft's intercom system with a stethoscope and headset system.

2. Description of the Prior Art

The use of stethoscopes is known in the prior art. More specifically, stethoscopes heretofore devised and utilized for the purpose of monitoring a parent's internal bodily vibrations are known to consist basically of familiar, expected and obvious structural configurations, notwithstanding the myriad of designs encompassed by the crowded prior art which have been developed for the fulfillment of countless objectives and requirements.

By way of example, U.S. Pat. No. 3,469,651 discloses an adjustable stethoscope earmuff shell. U.S. Pat. No. 4,975,967 to Rasmussen discloses an earplug for noise protected communication between the user of the earplug and surroundings. U.S. Pat. No. 5,010,890 to Pfohl et al. discloses a vital signs monitoring system. U.S. Pat. No. 5,099,519 to Guan discloses headphones.

While these devices fulfill their respective, particular objective and requirements, the aforementioned patents do not describe a stethoscope and headset system that allows a crew member of an aircraft to monitor a patient's internal bodily vibrations and communicate with other crew members through an aircraft's intercom system.

In this respect, the stethoscope and headset system according to the present invention substantially departs from the conventional concepts and designs of the prior art, and in doing so provides an apparatus primarily developed for the purpose of allowing a crew member of an aircraft to monitor a patient's internal bodily vibrations and communicate with other crew members through an aircraft's intercom system.

Therefore, it can be appreciated that there exists a continuing need for new and improved stethoscope and headset system which can be used for allowing a crew member of an aircraft to monitor a patient's internal bodily vibrations and communicate with other crew members through an aircraft's intercom system. In this regard, the present invention substantially fulfills this need.

SUMMARY OF THE INVENTION

In the view of the foregoing disadvantages inherent in the known types of stethoscopes now present in the prior art, the present invention provides an improved stethoscope and headset system. As such, the general purpose of the present invention, which will be described subsequently in greater detail, is to provide a new and improved stethoscope and headset system and method which has all the advantages of the prior art and none of the disadvantages.

To attain this, the present invention essentially comprises, in combination, a stethoscope. The stethoscope includes a rigid, hollow, and generally cylindrical housing having an open lower end and a sealed upper end. The stethoscope includes a diaphragm coupled within the lower end of the housing and extended therefrom for monitoring internal bodily vibrations of a patient when placed upon the patient's body. The stethoscope includes conversion circuitry disposed within the housing and coupled to the diaphragm for receiving the internal bodily vibrations within a range of sensitivities and transmitting internal bodily indication signals at strengths based upon the internal bodily vibrations. The stethoscope includes filter circuitry disposed within the housing and coupled to the conversion circuitry for controlling the range of sensitivities of the conversion circuitry to vibrations from the diaphragm with the filter circuitry having a user-orientable first slider switch extended from the housing with the first slider switch having one range of orientations for increasing the sensitivity of the conversion circuitry and having another range of orientations for decreasing the sensitivity of the conversion circuitry. The stethoscope includes volume control circuitry disposed within the housing and coupled to the conversion circuitry for receiving the internal bodily indication signals therefrom and transmitting the internal bodily indication signals at a controlled strength with the volume control circuitry having a user-orientable second slider switch extended from the housing with the second slider switch having one range of orientations for increasing the controlled strength of the internal bodily indication signals and another range of orientations for decreasing the controlled strength of the internal bodily indication signals. Lastly, the stethoscope includes a user-orientable power switch coupled to the conversion circuitry, filter circuitry, and volume control circuitry and extended from the housing with the power switch having one orientation for allowing the transmission of internal bodily indication signals from the stethoscope and another orientation for preventing such transmission.

A headset is provided. The headset includes an elongated, concave, and adjustable headband for placement on a user's head with the headband having two elongated strips slidably coupled together and a pad disposed therearound for cushioning a user's head when placed thereon. The headset includes a pair of essentially cylindrical and insulated earpieces with each earpiece coupled to a separate end of the headband and with each earpiece having an open interior end and a sealed exterior end. The headset includes a microphone coupled to one of the earpieces for receiving a user's voice and transmitting a plurality of intercom signals. Lastly, the headset includes a pair of speakers with each speaker coupled across the interior end of each earpiece for transmitting audible sounds upon actuation by internal bodily indication signals and intercom signals.

Lastly, a user-orientable selector switch is included and has lines extended therefrom coupled with the volume control circuitry of the stethoscope and the speakers and the microphone of the headset with the selector switch further coupleable with an intercom system of an aircraft. The selector switch has one orientation for allowing internal bodily indication signals to be transmitted to the speakers of the headset, thereby enabling a user to listen to a patient's internal bodily vibrations, and another orientation for allowing intercom signals to be received by and transmitted from the headset, thereby enabling a user to communicate through the intercom system.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved stethoscope and headset system which has all the advantages of the prior art stethoscopes and none of the disadvantages.

It is another object of the present invention to provide a new and improved stethoscope and headset system which may be easily and efficiently manufactured and marketed.

It is a further object of the present invention to provide a new and improved stethoscope and headset system which is of durable and reliable construction.

An even further object of the present invention is to provide a new and improved stethoscope and headset system which is susceptible of a low cost of manufacture with regard to both materials and labor, and which accordingly is then susceptible of low prices of sale to the consuming public, thereby making such a stethoscope and headset system economically available to the buying public.

Still yet another object of the present invention is to provide a new and improved stethoscope and headset system which provides in the apparatuses and methods of the prior art some of the advantages thereof, while simultaneously overcoming some of the disadvantages normally associated therewith.

Even still another object of the present invention is to provide a new and improved stethoscope and headset system for allowing a crew member of an aircraft to monitor a patient's internal bodily vibrations and communicate with other crew members through an aircraft's intercom system.

Lastly, it is an object of the present invention to provide a new and improved stethoscope and headset system comprising monitor means for monitoring internal bodily vibrations of a patient and conversion circuitry coupled to the monitor means for receiving the internal bodily vibrations and transmitting internal bodily indication signals based upon the internal bodily vibrations; a headset having a headband, a pair of earpieces coupled to the head band, a microphone for receiving a user's voice and transmitting a plurality of intercom signals, and a pair of speakers with each speaker coupled to an earpiece for transmitting audible sounds upon actuation by internal bodily indication signals and intercom signals; and a user-orientable selector switch coupled with the stethoscope and headset and coupleable with an intercom system of an aircraft, the selector switch having one orientation for enabling a user to listen to a patient's internal bodily vibrations and another orientation for enabling a user to communicate through the intercom system.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 1:
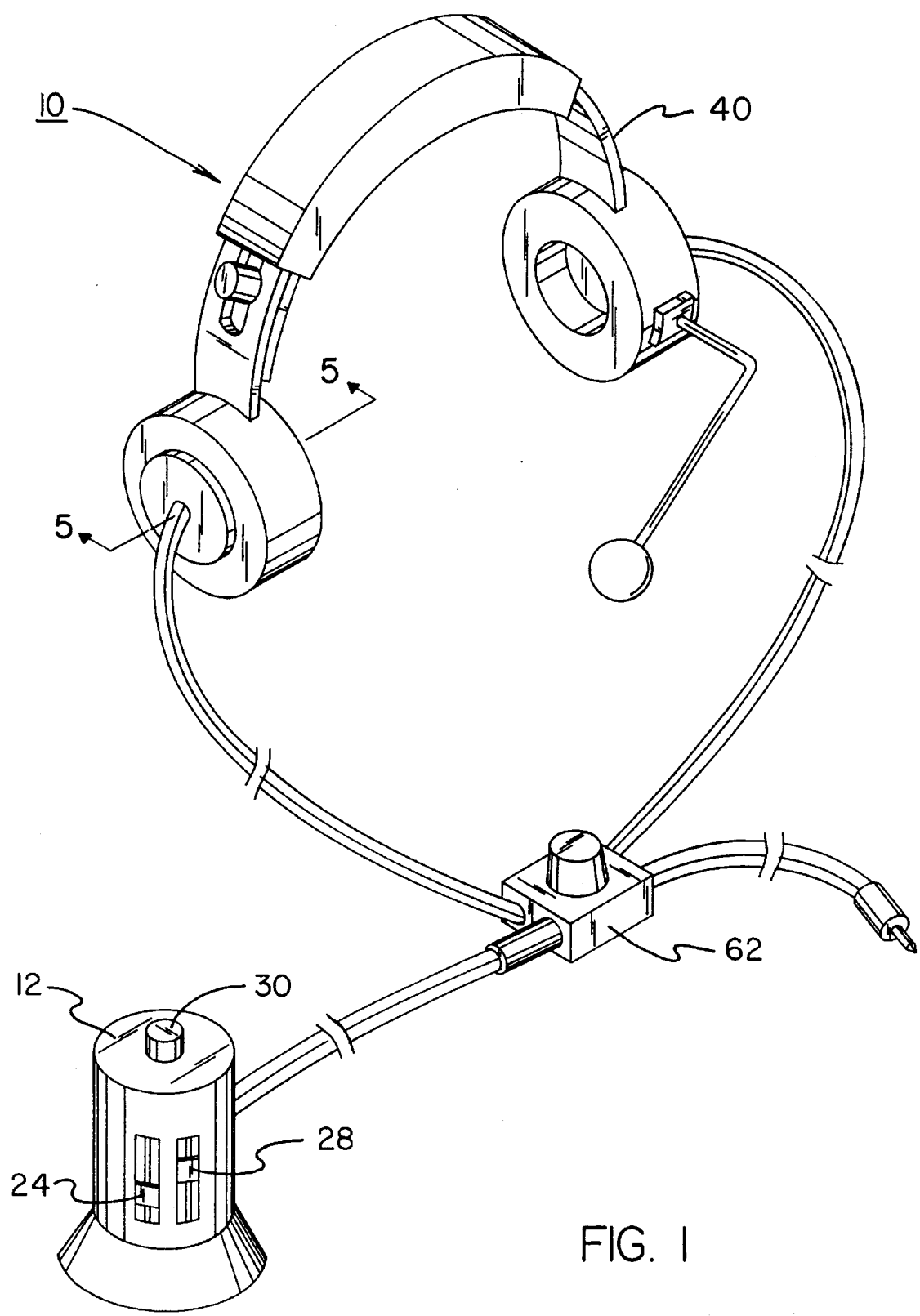
FIG. 1 is a perspective view of the preferred embodiment of the stethoscope and headset system constructed in accordance with the principles of the present invention.
Figure 2:
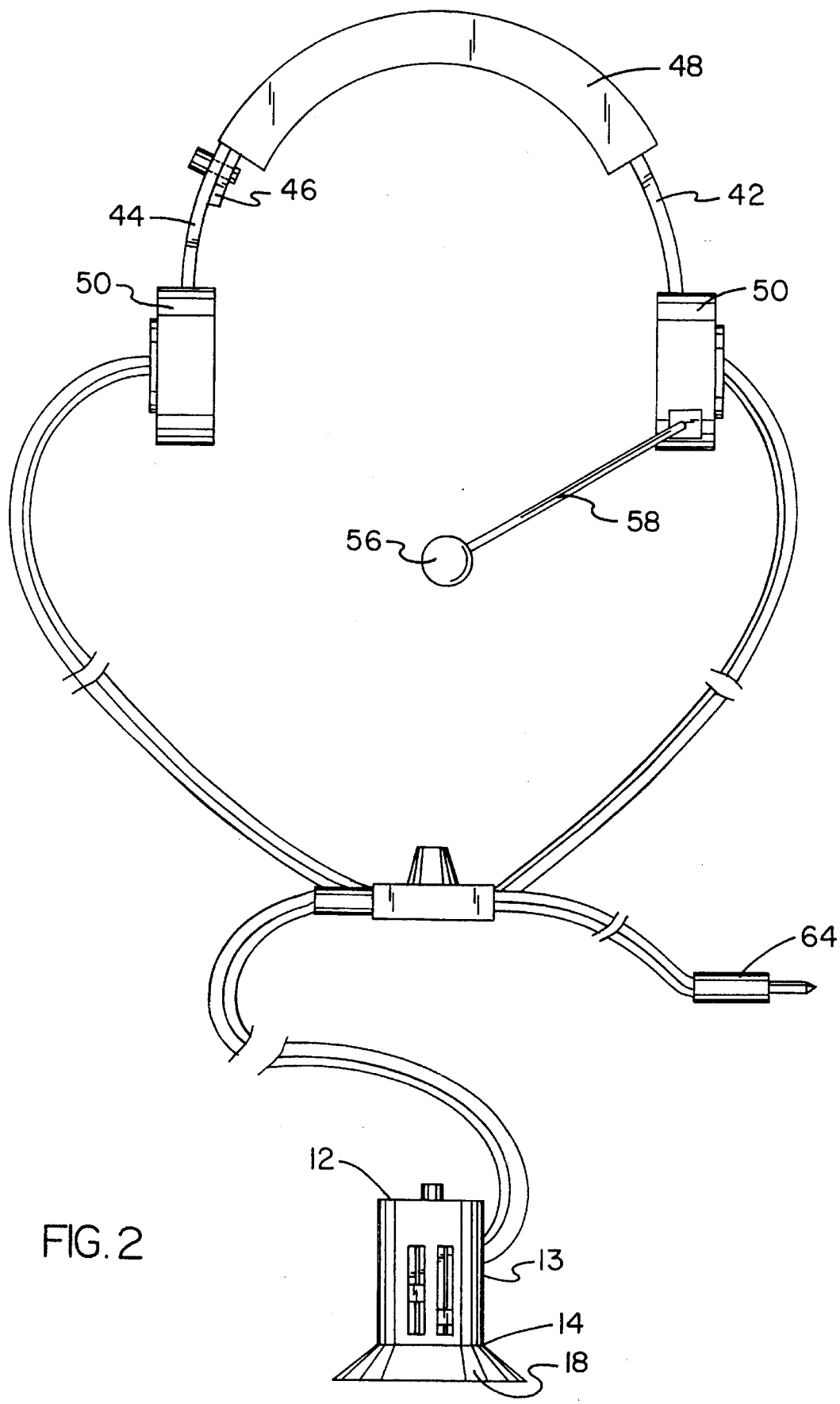
FIG. 2 is a side elevational view of the present invention shown in FIG. 1.
Figure 3:
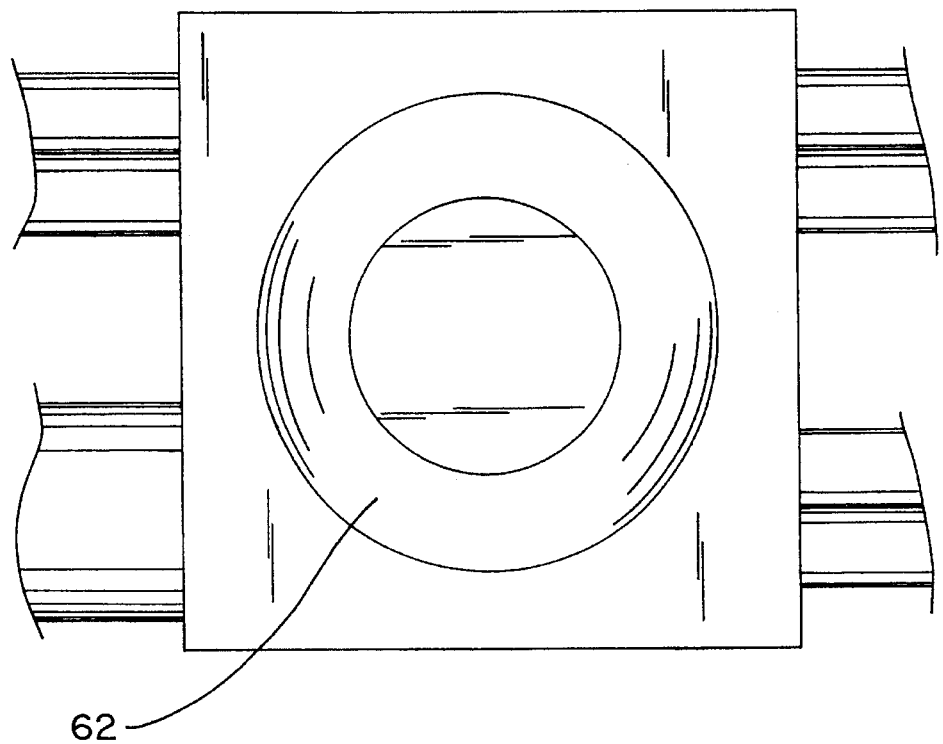
FIG. 3 is an enlarged view of the selector switch of the present invention.
Figure 4:
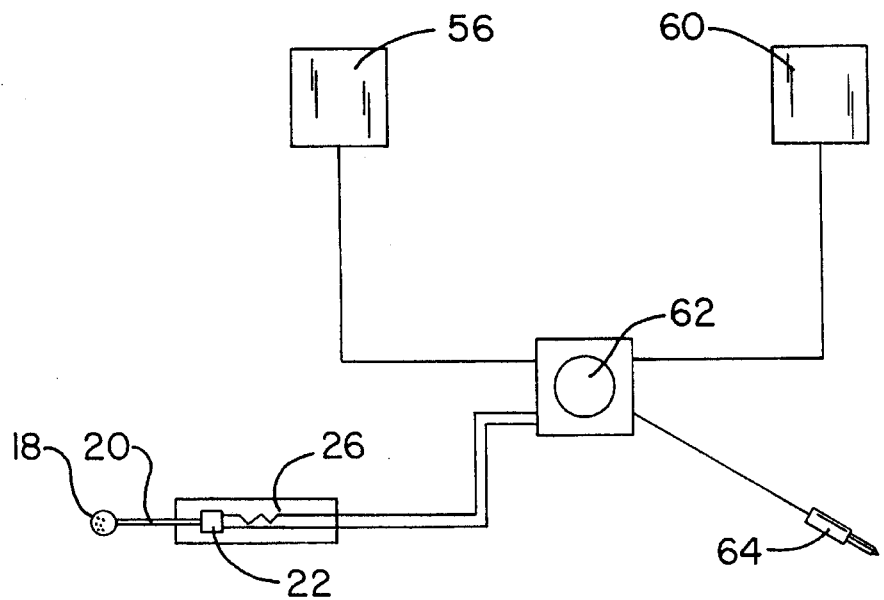
FIG. 4 is a schematic diagram of the present invention of FIG. 1.
Figure 5:
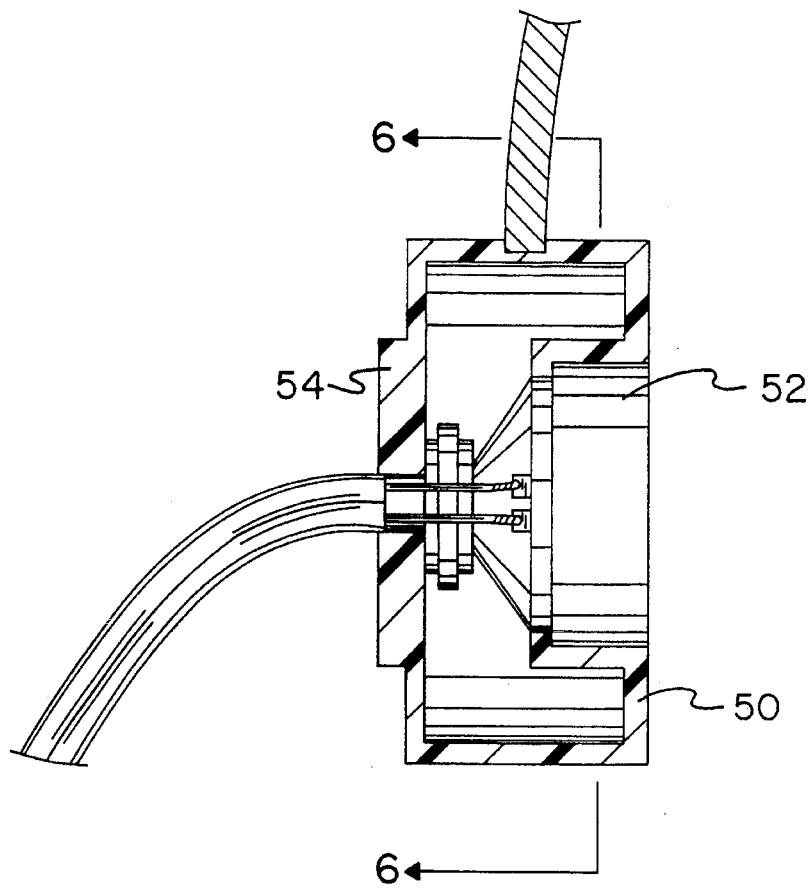
FIG. 5 is a cross-sectional view of an earpiece of the present invention taken along line 5—5 of FIG. 1.
Figure 6:
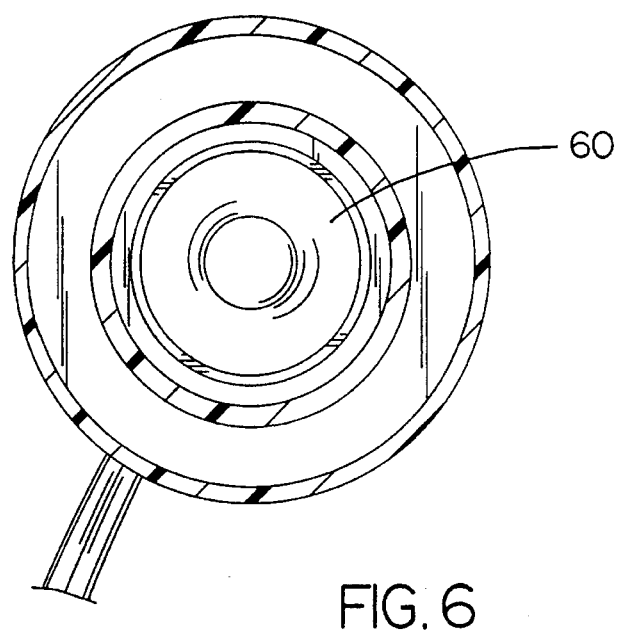
FIG. 6 is a cross-sectional view depicting the coupling between the speaker and an earpiece.

With reference now to the drawings, and in particular, to FIG. 1 thereof, the preferred embodiment of the new and improved stethoscope and headset system embodying the principles and concepts of the present invention and generally designated by the reference number 10 will be described.

Specifically, the present invention includes three major components. The major components are the stethoscope, headset, and selector switch. These components are interrelated to provide the intended function of monitoring internal bodily vibrations of a patient. These internal bodily vibrations include the sound of the patient's heartbeat, abdominal sounds such as those associated with the patient's lungs, and the sound of a patient's pulse discerned during a blood pressure check.

More specifically, it will be noted in the various Figures that the first major component is the stethoscope 12. The stethoscope is placed into operation when electrically energized with power supplied from an intercom system of an aircraft. The stethoscope includes six subcomponents. The subcomponents are the housing, diaphragm, conversion circuitry, filter circuitry, volume control circuitry, and power switch. These components are interrelated to allow the stethoscope to perform its intended function.

The first subcomponent of the stethoscope is the housing 13. The housing is rigid, hollow and generally cylindrical in structure. It is formed of metal, plastic, or other rigid material. The housing has an open lower end 14 and an upper sealed end 16. The housing serves as the main support for holding the remaining subcomponents of the stethoscope in a fixed configuration.

The second subcomponent of the stethoscope is the diaphragm 18. The diaphragm is coupled within the lower end 14 of the housing. It is extended from the housing and adapted for receiving internal bodily vibrations. It is enabled for receiving internal bodily vibrations when placed upon a patient's body.

The third subcomponent of the stethoscope is the conversion circuitry 20. The conversion circuitry is disposed within the housing 13. The conversion circuitry is also coupled to the diaphragm 18 for receiving the internal bodily vibrations within a range of selected sensitivities. The conversion circuitry transmits internal bodily indication signals at strengths based upon the internal bodily vibrations. These internal bodily indications are embodied in the form of electrical signals.

The fourth subcomponent of the stethoscope is the filter circuitry 22. The filter circuitry is disposed within the housing 13. The filter circuitry is also coupled to the conversion circuitry 20. The filter circuitry is used for controlling the range of sensitivities of the conversion circuitry to vibrations of the diaphragm 18. The filter circuitry has a user-orientable first slider switch 24. This slider switch is extended from the housing 13. The first slider switch has one range of orientations for increasing the sensitivity of the conversion circuitry and another range of orientations for decreasing the sensitivity of the conversion circuitry. By increasing the sensitivity of the conversion circuitry, even faint internal bodily vibrations may be converted to internal bodily indication signals. Sensitivity selections is performed by a user moving the first slider switch either one way or the other. The filter circuitry essentially serves as an equalizer for the present invention, allowing a user to enhance or dampen various bodily vibrations.

The fifth subcomponent of the stethoscope is the volume control circuitry 26. The volume control circuitry is disposed within the housing 13. The volume control circuitry is also coupled to the conversion circuitry for receiving the internal bodily indication signals therefrom. The volume control circuitry then transmits the internal bodily indication signals at a controlled strength. The volume control circuitry has a user orientable second slider switch 28. The second slider switch is extended from the housing 13. The second slider switch has one range of orientations for increasing the controlled strength or volume of the internal bodily indication signals and another range of orientations for decreasing the controlled strength or volume of the internal bodily indication signals. Essentially, the strength or volume of the internal bodily indication signals are increased through amplification components of the volume control circuitry. Likewise, the strength or volume of the internal bodily indication signals are decreased through resistive components of the volume control circuitry.

The sixth subcomponent of the stethoscope is the power switch 30. The power switch is extended upwards from the upper end 16 of the housing 13. The power switch is adapted to be oriented by a user. The power switch is coupled to the conversion circuitry 20, filter circuitry 22, and volume control circuitry 26. The power switch is also adapted to receive power through an intercom system of an aircraft. The power switch has one orientation for allowing the transmission of internal bodily indication signals from the stethoscope and another orientation for preventing such transmission. Transmission of internal bodily indication signals is allowed or prevented by energizing or de-energizing the conversion circuitry, filter circuitry, and volume control circuitry through the power switch.

The second major component is the headset 40. The headset is placed into operation when electrically energized through power supplied from an intercom system of an aircraft. The headset includes four subcomponents. The subcomponents are the headband, earpieces, microphone, and speakers. These components are interrelated to allow the headset to perform its intended function.

The first subcomponent of the headset is the headband 42. The headband is elongated, concave, and adjustable for placement on a user's head. The headband has two elongated strips 44, 46 slidably coupled together. The headband also includes a pad 48 disposed around the strips for cushioning a user's head.

The second subcomponent of the headset is the earpieces 50. The present invention includes a pair of earpieces. The earpieces are essentially cylindrical in structure, but may also be formed in other configurations that are securable over a user's ear. They are formed with an insulative material for shielding noise damaging to a user's ear. Each earpiece is coupled to a separate end of a headband and extended downwards therefrom. Each earpiece has an open interior end 52 and a sealed exterior end 54. The earpieces in combination with the headband form an earmuff-type configuration.

The third subcomponent of the headset is the microphone 56. The microphone is coupled to one of the earpieces 50. The microphone includes a boom 58 extended downwards for allowing it to be placed near a user's mouth. The microphone is adapted to be actuated by a user's voice and transmit a plurality of intercom signals upon such actuation. These intercom signals are embodied in the form of electrical signals.

The fourth subcomponent of the headset is the speakers 60. The present invention includes a pair of speakers. Each speaker is coupled across the interior end 52 of each earpiece 50. Each speaker transmits audible sounds upon actuation by internal bodily indication signals and intercom signals. The loudness of sounds generated by the speakers is based upon the strength of the internal bodily indication signals and strength of the intercom signals received. Therefore, the loudness or volume of a patient's internal bodily vibrations is essentially controlled through the second slider switch 28 of the stethoscope 12. The speaker is conventional in design and commercially available. In an alternate embodiment, the speakers are secured in ear plugs insertable directly into a user's ears.

The third major component is the selector switch 62. The selector switch is orientable by a user. The selector switch has electrically conductive lines extended therefrom and coupled with the volume control circuitry 26 of the stethoscope and the speakers 60 and the microphone 56 of the headset. The selector switch is further coupleable with an intercom system of an aircraft through a male plug 64. In this fashion, electrical power may be received through the male plug as well as intercom signals generated by other crew members through their microphones. The selector switch has one orientation for allowing internal bodily indication signals to be transmitted to the speakers 60 of the headset. In this instance, a user may listen to a patient's internal bodily vibrations. The selector switch also has another orientation for allowing intercom signals to be received and transmitted from the headset 40. The user is then able to communicate with other aircraft crew members through the intercom system.

The present invention is designed for use in areas which are subjected to very high levels of noise. A typical example of its utility would be in evacuation aircraft used by the military. The craft is often a helicopter whose interior is filled with the sounds of the roar of the engines and the thrashing of the propeller blades. Personnel within the craft and those in the surrounding area are required to wear protective headgear to prevent damaging their hearing. In the short time required to remove the protection and apply a stethoscope on the patient, a person's hearing may be damaged irreparably. Furthermore, if a conversation must also be carried on with other crew members, the problems are further multiplied. In this case, the earpieces of a conventional prior art stethoscope must be removed to listen to a crew member, and the acuity of the hearing is immediately affected, just when it is most needed-trying to detect problems with a patient's internal bodily vibrations through the stethoscope. The present invention is also useable in any other environment where noisy background conditions prevail such as an ambulance.

By combining an intercom unit into a stethoscope as with the present invention, the earpiece can always remain attached to a user's ears. A user can listen using the stethoscope and switch directly over to the intercom system to carry on a conversation. This is accomplished through a selector switch without removing any gear. The microphones and speakers are in the headset, and the unit is plugged into the intercom system. The earpieces secured over a user's ears prevent the outside sounds from interfering with communication. In the present invention, the intercom can override the stethoscope to convey emergency or very important information.

Although electronic stethoscopes exist, it is not practical for a user to remove his conventional headset or helmet/headset unit and then expose his ears to dangerously high noise levels during the time it takes for the user to place the earpieces of a conventional prior art electronic stethoscope in his ears. In doing so, the possibility of a user damaging his ears has greatly increased. Furthermore, a user loses valuable hearing acuity while trying to listen to a patient's internal bodily vibrations using a conventional stethoscope during an examination under these high noise conditions. In addition, conventional electronic stethoscopes do not have the additional ear protection (muffling quality through the use of the earpieces) like the present invention, and the earpieces of the present invention could be formed to snap out of the headset and be used with a conventional headset or helmet headset.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A stethoscope and headset system for allowing a crew member of an aircraft to monitor a patient's internal bodily vibrations and communicate with other crew members through an aircraft's intercom system comprising, in combination;

a stethoscope further comprising:
a rigid, hollow, and generally cylindrical housing having an open lower end and a sealed upper end;
a diaphragm coupled within the lower end of the housing and extended therefrom for monitoring internal bodily vibrations of a patient when placed upon the patient's body;
conversion circuitry disposed within the housing and coupled to the diaphragm for receiving the internal bodily vibrations within a range of sensitivities and transmitting internal bodily indication signals at strengths based upon the internal bodily vibrations;
filter circuitry disposed within the housing and coupled to the conversion circuitry for controlling the range of sensitivities of the conversion circuitry to vibrations from the diaphragm, the filter circuitry having a user-orientable first slider switch extended from the housing with the first slider switch having one range of orientations for increasing the sensitivity of the conversion circuitry and having another range of orientations for decreasing the sensitivity of the conversion circuitry;
volume control circuitry disposed within the housing and coupled to the conversion circuitry for receiving the internal bodily indication signal's therefrom and transmitting the internal bodily indication signals at a controlled strength, the volume control circuitry having a user-orientable second slider switch extended from the housing with the second slider switch having one range of orientations for increasing the controlled strength of the internal bodily indication signals and another range of orientations for decreasing the controlled strength of the internal bodily indication signals; and
a user-orientable power switch coupled to the conversion circuitry, filter circuitry, and volume control circuitry and extended from the housing with the power switch having one orientation for allowing the transmission of internal bodily indication signals and another orientation for preventing such transmission;

a headset further comprising;
an elongated, concave, and adjustable headband for placement on a user's head, the headband having two elongated strips slidably coupled together and a pad disposed therearound for cushioning a user's head when placed thereon;
a pair of essentially cylindrical and insulated earpieces, each earpiece coupled to a separate end of the headband, each earpiece having an open interior end and a sealed exterior end;
a microphone coupled to one of the earpieces for receiving a user's voice and transmitting a plurality of intercom signals; and a pair of speakers, each speaker coupled across the interior end of each earpiece for transmitting audible sounds upon actuation by internal bodily indication signals and intercom signals; and a user-orientable selector switch having lines extended therefrom coupled with the volume control circuitry of the stethoscope and the speakers and the microphone of the headset, the selector switch further coupleable with an intercom system of an aircraft, the selector switch having one orientation for allowing internal bodily indication signals to be transmitted to the speakers of the headset, thereby enabling a user to listen to a patient's internal bodily vibrations, the selector switch having another orientation for allowing intercom signals to be received by and transmitted from the headset, thereby enabling a user to communicate through the intercom system;

whereby the intercom overrides the stethoscope for allowing the conveyance of emergency information and further the stethoscope is coupled to the intercom system for allowing electrical power received therefrom to be supplied to the stethoscope.

* * * * *